United States Patent
Kim et al.

(10) Patent No.: US 8,027,036 B2
(45) Date of Patent: Sep. 27, 2011

(54) APPARATUS FOR DETECTING PARTICLES ON A GLASS SURFACE AND A METHOD THEREOF

(75) Inventors: Hyunwoo Kim, Asan-si (KR); Youngchae Ko, Cheoan-si (KR); Sungjong Pyo, Asan-si (KR); Taeho Keem, Cheoan-si (KR)

(73) Assignee: Samsung Corning Precision Materials Co., Ltd., Jinpyeong-Dong, Gumi-Si, Gyeingsangbuk-Do (KR)

( * ) Notice: Subject to any disclaimer, the term of this patent is extended or adjusted under 35 U.S.C. 154(b) by 88 days.

(21) Appl. No.: 12/417,318

(22) Filed: Apr. 2, 2009

(65) Prior Publication Data

US 2010/0214564 A1    Aug. 26, 2010

(30) Foreign Application Priority Data

Feb. 20, 2009    (KR) .................. 10-2009-0014186

(51) Int. Cl.
*G01N 21/00* (2006.01)
*G01N 21/47* (2006.01)
(52) U.S. Cl. ..................... 356/337; 356/237.1
(58) Field of Classification Search .... 356/327.1–237.5, 356/239.1, 239.3, 239.8; 250/559.11, 559.41, 250/559.45, 559.16, 559.09, 561–563
See application file for complete search history.

(56) References Cited

U.S. PATENT DOCUMENTS

| | | | | |
|---|---|---|---|---|
| 3,814,946 A | * | 6/1974 | Takahashi et al. | 250/559.45 |
| 4,492,477 A | * | 1/1985 | Leser | 356/430 |
| 4,669,875 A | * | 6/1987 | Shiba et al. | 356/237.3 |
| 4,886,975 A | * | 12/1989 | Murakami et al. | 250/559.41 |
| 4,999,511 A | * | 3/1991 | Kohno | 250/559.11 |
| 5,359,407 A | * | 10/1994 | Suzuki et al. | 356/237.2 |
| 5,381,225 A | * | 1/1995 | Kohno | 356/237.5 |
| 5,963,316 A | * | 10/1999 | Miura et al. | 356/237.3 |
| 6,166,808 A | * | 12/2000 | Greve | 356/601 |
| 6,204,917 B1 | * | 3/2001 | Smedt | 356/237.5 |
| 7,420,671 B2 | * | 9/2008 | Sonda | 356/239.1 |

FOREIGN PATENT DOCUMENTS

| | | | |
|---|---|---|---|
| JP | 05223733 A | * | 8/1993 |
| JP | 09-089793 | | 4/1997 |
| JP | 2001-159613 | | 6/2001 |
| JP | 2005-009995 | | 1/2005 |
| JP | 2007-163137 | | 6/2007 |
| JP | 2008-039444 | | 2/2008 |

* cited by examiner

*Primary Examiner* — Sang Nguyen
(74) *Attorney, Agent, or Firm* — Lexyoume IP Group, PLLC

(57) ABSTRACT

The present invention relates to an apparatus for detecting particles on a glass surface and a method thereof, and more specifically, to an apparatus for detecting particles on a glass surface and a method thereof for exactly inspecting particles which may be created on a glass surface where micro circuits are deposited. The apparatus for detecting the particles on the glass surface in accordance with the present invention comprises laser beam irradiators for detecting particles on a glass substrate on upper and lower sides of the glass substrate at certain intervals, respectively, and wherein the irradiators are configured so that beams emitted from the laser beam irradiators can be irradiated in a direction vertical to a transferring direction of the glass substrate, thereby exactly detecting particles detached to the glass surface without exception.

11 Claims, 7 Drawing Sheets

(a)

(b)

(a)

(b)

APPARATUS FOR DETECTING PARTICLES ON A GLASS SURFACE AND A METHOD THEREOF

BACKGROUND OF THE INVENTION

1. Field of the Invention

The present invention generally relates to an apparatus for detecting particles on a glass surface and a detecting method thereof, and more specifically, to an apparatus for detecting particles on a glass surface and a detecting method thereof for exactly inspecting particles on a surface where micro circuit patterns are deposited, regardless of flatness.

2. Description of the Related Art

When particles exist on a glass surface used for a flat display and micro circuit patterns are deposited on these particles, it causes deterioration of the micro circuit patterns. Thus, before the micro circuit patterns are deposited, it should check whether any particles exist on a provided glass substrate (particularly, a glass surface where circuits are deposited).

Since the inspection on the surface of the glass substrate is conducted by using a camera while the glass substrate is being transferred, exact inspection is essential even though flatness of the glass substrate, which is caused during the transferring, changes. Therefore, in a prior detecting apparatus, an automatic distance adjustment device was additionally used to irradiate very thin laser illumination by giving a large slope in the transferring direction of the glass substrate, and to compensate changes of flatness of the glass substrate. The prior detecting apparatus for particles, however, has some restrictions on deciding whether particles are attached to a glass surface (upper side) where circuits are deposited, or to a glass surface (lower side) where the circuits are not deposited. Furthermore, accuracy of inspection was influenced by the changes of the flatness of the glass substrate.

SUMMARY OF THE INVENTION

It is therefore an object of the present invention to provide an apparatus for detecting particles on a glass surface and a method thereof for exactly inspecting particles which may be created on a glass surface where micro circuits are deposited.

It is another object of the present invention to provide an apparatus for detecting particles on a surface of a glass substrate and a method thereof for exactly inspecting particles which may be created on a glass surface, without an additional device such as an automatic distance adjustment device even though flatness of transferring glass changes.

To achieve the above object, an apparatus for detecting particles on a glass surface in accordance with the present invention, comprising:

an upper laser beam irradiator for irradiating laser beams, which are irradiated from one upper side of the glass substrate and reach the other upper side; an upper detection camera for receiving beams scattered by particles after the laser beams irradiated in the upper laser light irradiator are irradiated on an upper side of the glass substrate; a lower laser beam irradiator for irradiating laser beams, which are irradiated from one lower side of the glass substrate and reach the other lower side; a lower detection camera for receiving beams scattered by particles after the laser beams irradiated in the lower laser beam irradiator are irradiated on a lower side of the glass substrate; and a detection signal processor for deciding positions of the particles on the glass substrate by analyzing image signals outputted from the upper detection camera and the lower detection camera.

According to an apparatus for detecting particles on a glass surface and a method thereof in accordance with the present invention, it is possible to exactly detect particles attached to the glass substrate without exception, and to exactly perceive whether the particles are created on a glass surface where circuits are deposited or on a glass surface where the circuits are not deposited.

In addition, according to an apparatus for detecting particles on a glass surface and a method thereof in accordance with the present invention, it can more exactly check whether particles are created, irrespective of flatness of a glass substrate, and cut down facility investment costs since an automatic distance adjustment device used in a prior apparatus is not needed, not to mention much easier facility maintenance and repair works. Besides, an illuminating method of the present invention has an advantage of irradiating a wider area with one illumination, compared to the prior art.

BRIEF DESCRIPTION OF THE DRAWINGS

The advantages of the invention will become readily apparent to those skilled in the art from the following detailed description of a preferred embodiment when considered in the light of the accompanying drawings, in which.

DETAILED DESCRIPTION OF PREFERRED EMBODIMENTS

An apparatus for detecting particles on a glass surface in accordance with the present invention comprises an upper laser beam irradiator (51) for detecting particles of a glass substrate (30) on one upper side of the glass substrate, and comprises a lower laser beam irradiator (53) on one lower side of the glass substrate (30) at certain intervals from a spot where the upper laser beam irradiator is disposed, respectively, and wherein laser beams emitted from the laser beam irradiators (51,53) are irradiated from one side of the glass substrate (30), respectively, and reach the other side thereof, and at this time, it is desirable to make the laser beams irradiated in a direction vertical to the transferring direction of the glass substrate (30), thereby exactly detecting particles attached to a surface of the glass substrate without missing and easily perceiving on which side of the glass substrate (30) the particles exist.

Hereinafter, a desirable embodiment of an apparatus for detecting particles of a glass surface in accordance with the present invention will be fully described in reference to the accompanied drawings.

Before explanation, the one side where the upper laser beam irradiator (51) and the lower laser beam irradiator (53) are individually disposed indicates one of two edge portions located side by side in the transferring direction of the glass substrate (30), among four edges of the glass substrate (30) arranged in rectangular shape, and the other side means the other of the two edge portions as an edge portion located in opposition to the one side.

Figure 1:
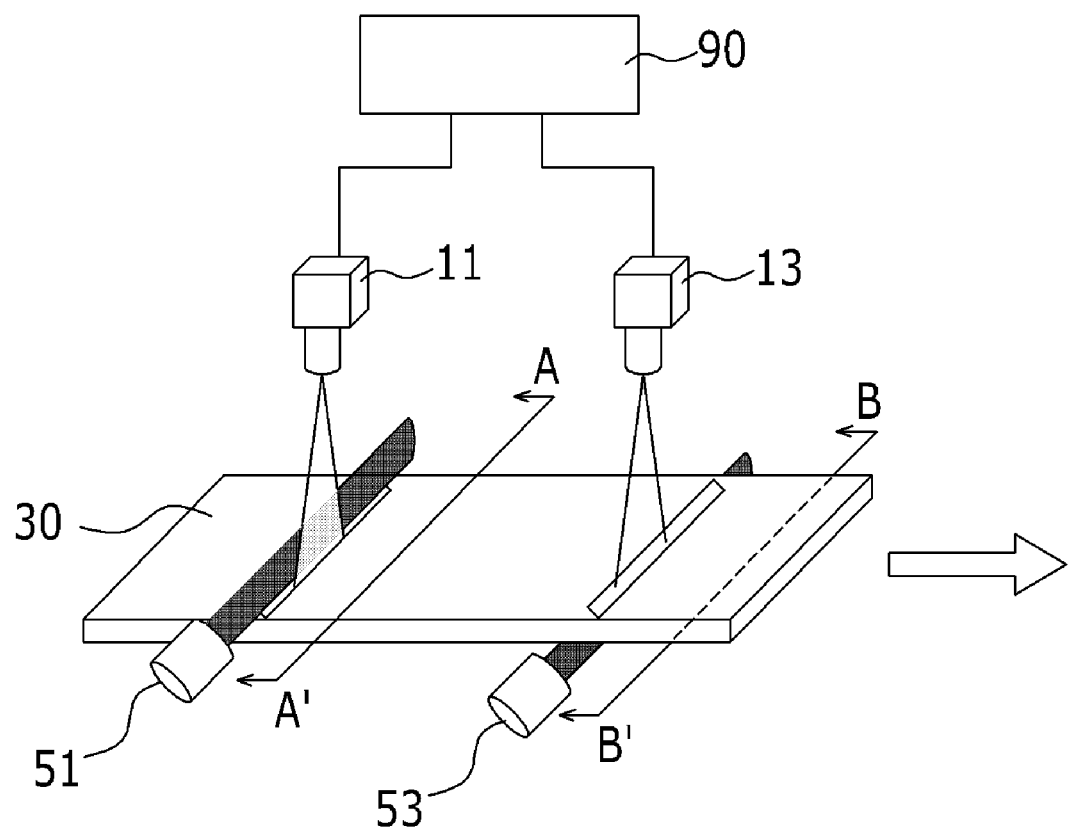
FIG. 1 is a format diagram of roughly illustrating a desirable embodiment of an apparatus for detecting particles on a glass surface in accordance with the present invention.
Figure 2A:
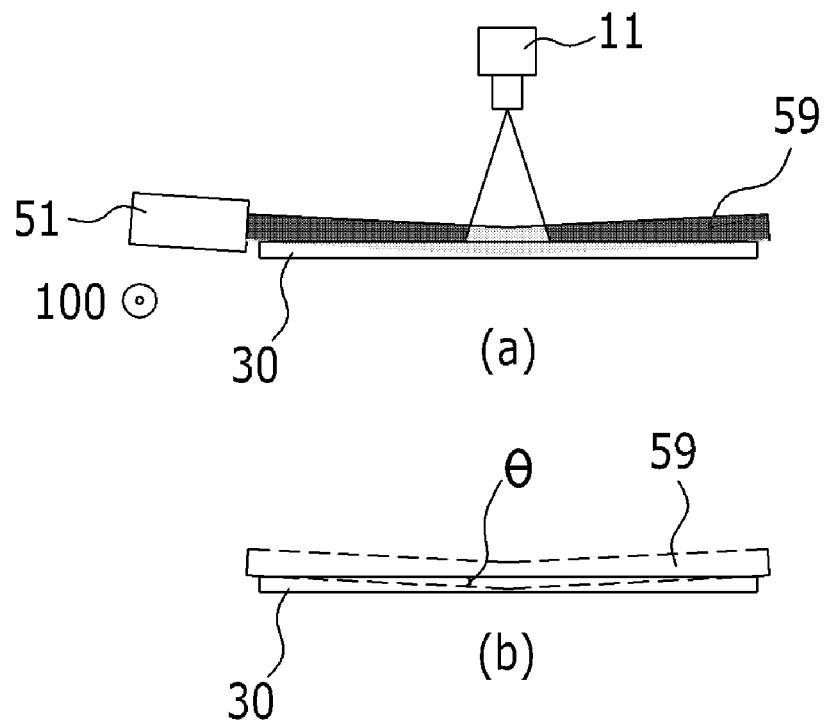
FIG. 2a is a sectional view of A-A' direction of FIG. 1.

FIG. 1 is a format diagram of roughly illustrating a desirable embodiment of an apparatus for detecting particles on a glass surface in accordance with the present invention, and FIG. 2a is a sectional view of A-A' direction of FIG. 1.

Referring to FIG. 1 and FIG. 2, the apparatus for detecting the particles on the glass surface in accordance with the present invention comprises: an upper laser beam irradiator (51) for irradiating a laser beam which is irradiated from one upper side of a glass substrate (30) and arrives up to the other upper side; an upper detection camera (11) for receiving a laser beam diffused by particles existing on the glass substrate (30) after a laser beam (59) irradiated from the upper laser beam irradiator (51) is irradiated on an upper side of the glass substrate (30); a lower laser beam irradiator (53) for irradiating a laser beam which is irradiated from one lower side of the glass substrate (30) and arrives up to the other lower side; a lower detection camera (13) for receiving a laser beam diffused after the laser beam irradiated from the lower laser beam irradiator (53) is irradiated on a lower side of the glass substrate (30); and a detection signal processor (90) for deciding on information about particles attached to an upper side or a lower side based on image signals inputted from the upper detection camera (11) and the lower detection camera (13).

Besides, the laser beams individually outputted from the upper laser beam irradiator (51) and the lower laser beam irradiator (53) are irradiated by crossing one side of the glass substrate until reaching the other side from the one side of the glass substrate (30) like shown above, and at this time, it is desirable that the laser beams are irradiated in a direction vertical to the transferring direction of the glass substrate (30).

The glass substrate (30) is made of a thin glass material used for a panel of a display device such as an LCD, and is generally in 0.5 to 0.7 mm thickness. One side (hereinafter, an upper side) is deposited with micro circuit patterns, while the other side (hereinafter, a lower side) in opposition to the one side exists as a side where the circuit patterns are not formed.

A reference numeral "100" shows the transferring direction of the glass substrate (300).

The laser beam irradiators (51,53) consist of the upper laser beam irradiator (51) for irradiating a laser beam on the upper side of the glass substrate (30), and the lower laser beam irradiator (53) for irradiating a laser beam on the lower side, and it is desirable that the laser beams irradiated on the upper and lower sides of the glass substrate are in approximately 100 mm width and 0.65 mm to 0.95 mm thickness when outputted from the laser beam irradiators.

Furthermore, it should make clear that the laser beams' width (about 100 mm) explained in the above is desirable for the glass substrate (30) of roughly 1 m width, and the width is not limited to 1 m.

For example, given that the process glass substrate (30) is the glass substrate (30) of more than 1 m width, it is desirable that the above laser beams are in more than 100 mm width. And, in case the process glass substrate (30) is in less than 1 m width, it is desirable to configure the laser beams in less than 100 mm width.

The upper laser beam irradiator (51) is a unit for detecting particles attached to the upper side of the glass substrate (30), and the laser beam (59) outputted from the upper laser beam irradiator (51) is incident on the upper side of the glass substrate (30) with predetermined thickness and width.

Figure 7:
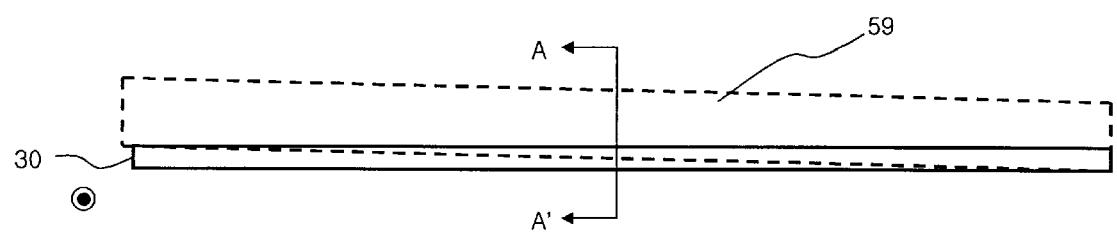
FIG. 7 is a diagram for illustrating the shape of laser beam according to the present invention.
Figure 7:
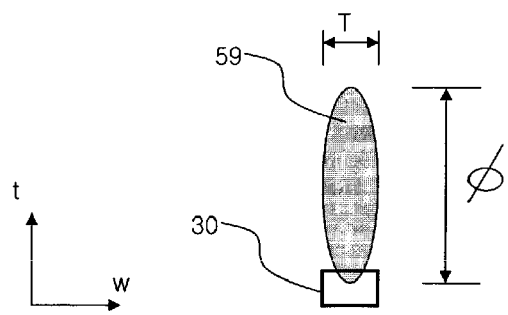

FIG. 7 is a diagram for illustrating the shape of a laser beam used in the present invention.

Like shown in FIG. 7(a), a laser beam (59) is being irradiated on a side of an upper side of the glass substrate (30) which is being transferred to a front side of the drawing, and FIG. 7(b) shows an A-A' sectional view of FIG. 7(a). Like shown in FIG. 7(b), when inspecting particles of a glass substrate (30) whose flatness is not regular, it is better for a laser beam (59) to have an oblong shape of a small thickness (T) in width direction (w) of the glass substrate (30) and of a broad width (Φ) in height direction (t).

Moreover, it is better for the laser beam (59) to be irradiated by enabling a surface corresponding to the width of the laser beam to formulate at least 60° inclination (desirably, the surface forms a perpendicular line on the glass substrate (30)) from one side of the glass substrate (30).

Specific features of the laser beam (59) incident on the upper side of the glass substrate (30) will be described as follows.

Like shown in FIG. 1, FIG. 2a (a), the upper laser beam (59) outputted from the upper laser beam irradiator (51) is irradiated in a direction vertical to a transferring direction of the glass substrate (30), and at this time, a whole surface of an upper-side area of the glass substrate (30) located in an area of the upper laser beam irradiated on the glass substrate (30) should be included inside the laser beam. Likewise, it is desirable that a lower-side area in opposition to the upper-side area is irradiated without being included in the inside of the laser beam as much as possible.

It is to minimize an amount of the laser beam (59), which is transmitted to the lower side by being incident on the upper side, so that signal strength of the laser beam diffused by particles located on the upper side is transmitted to the lower side in order to make the signal strength much larger than signal strength of the laser beam diffused by particles located on the lower side, thereby perfectly detecting the particles existing on the upper and lower sides of the glass substrate (30) by distinguishing them.

Therefore, the most ideal irradiation angle of the upper laser beam matched with the above purpose is such that, when the upper laser beam is incident in parallel to the glass substrate (30), it is necessary for the upper laser beam (59) to be irradiated to include a whole area, on which the laser beam (59) is incident, in the inside of the upper laser beam (59) on the upper side of the glass substrate (30), and to prevent a lower-side area from being included in the inside of the upper laser beam.

However, if the laser beam is irradiated in parallel with the glass substrate (30) like above, it is possible to magnify precision that detects the particles existing on the upper and lower sides by perfectly distinguishing them, but the following disadvantages may be created.

That is to say, the transferred glass substrate (30) can experience changes of flatness of the glass substrate (30) while being transferred to detect particles, owing to curving of a transferring device and the glass substrate (30) itself.

Accordingly, when the upper laser beam (59) is irradiated in parallel to the glass substrate (30) like above, due to the aforementioned changes of the flatness of the glass substrate (30), 1) the upper side of the glass substrate (30) may be deviated without being included in the inside of the upper laser beam, or 2) even the lower side as well as the upper side is included in the inside of the upper laser beam (59).

In the case of 1), there is a problem that particles may just pass without being detected even though they exist on the upper side of the glass substrate (30), and 2) has a problem that the particles existing on the upper side are detected or displayed in similar signal strength by both an upper detection camera (11) and a lower detection camera (13) which are to be explained later, therefore it may be difficult to distinguish on which side of the glass substrate (30) the detected particles exist.

To solve such problems, like shown in FIG. 2a (b), a laser beam in accordance with a desirable embodiment of the present invention is configured to be diagonally irradiated as formulating a predetermined inclination angle (θ) from the upper side of the glass substrate (30), while the inclination angle (θ) is incident at a low angle between 0.06° and 6° angles.

The inclination angle (θ) is an irradiation angle which considers a degree of flatness changes which may occur on the transferred glass substrate (30). When the upper laser beam (59) is irradiated on the upper side of the glass substrate (30) as formulating a low-degree irradiation angle in such a range, the upper side of the glass substrate (30) can be maintained in a state of being included in the inside of the upper laser beam all the time even though the flatness changes occur on the glass substrate (30).

Furthermore, since the inclination angle is configured as a low angle between 0.06° and 6° angles, most of the upper laser beam (59) incident on the upper side of the glass substrate (30) are reflected to enable an amount of a beam which transmits the glass substrate (30) to get very smaller, thereby minimizing diffusion of the transmitted upper laser beam, which occurs by particles existing on the lower side. Accordingly, it can perfectly detect particles existing on the upper and lower sides by distinguishing them.

Figure 6:
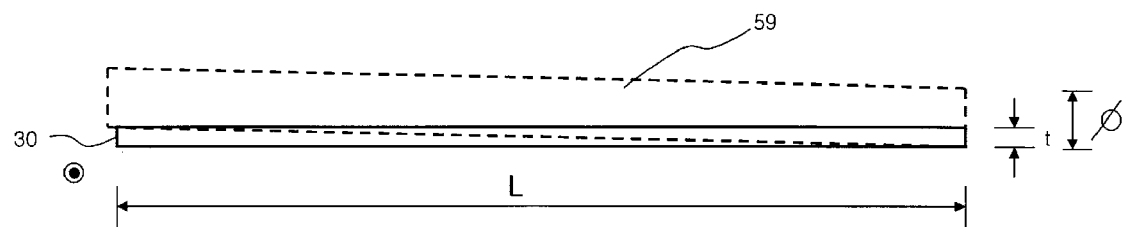
FIG. 6 is a diagram for illustrating preferable irradiation angle of laser beam according to the present invention.
Figure 6:
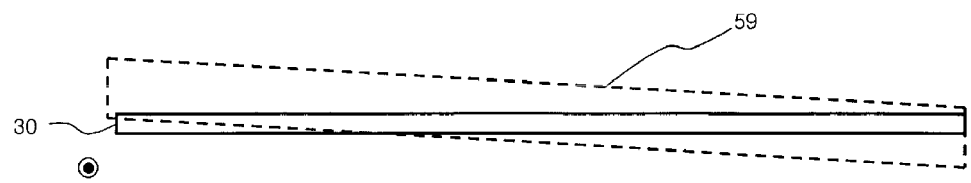

From now on, the inclination angle with 0.06° to 6° will be more specifically described in reference to FIG. 6. For explanatory convenience, suppose that thickness (t) of a glass substrate (30) is 1 mm, width (L) of the glass substrate (30) is 1,000 mm, and width (Φ) of a laser beam is 100 mm. Such numerical values are not largely different from those of substantially produced equipment or glass. Like shown in FIG. 6(a), when a lower part of a laser beam (59) is contacted with an opposite lower side of the glass substrate (30), the lowest angle is maintained. And, like shown in FIG. 6(b), if an upper part of the laser beam (59) is contacted with an opposite upper side of the glass substrate (30), the highest angle is maintained. In FIG. 6(a), an angle between the laser beam (59) and a glass surface is roughly 0.06°, and in FIG. 6(b), an angle between the laser beam (59) and a glass surface is approximately 6°.

Thus, it is desirable that the laser beam (59) in accordance with the present invention is irradiated at a low angle as maintaining the angle of 0.06° to 6° with the glass surface.

The upper detection camera (11) receives a beam diffused by particles existing on the glass substrate (30), after the upper laser beam (59) emitted from the upper laser beam irradiator (51) is irradiated on an upper side of the glass substrate (30).

More specifically, the upper detection camera (11) is a CCD (Charge-Coupled Device) for obtaining an image by receiving the diffused beam and changing it into an electric charge, and the CCD produces a detection image signal by reconfiguring information with the use of an amount of electrons generated according to an amount of photons received in a photo diode, then the detection image signal is transmitted to the detection signal processor (90).

Figure 2B:
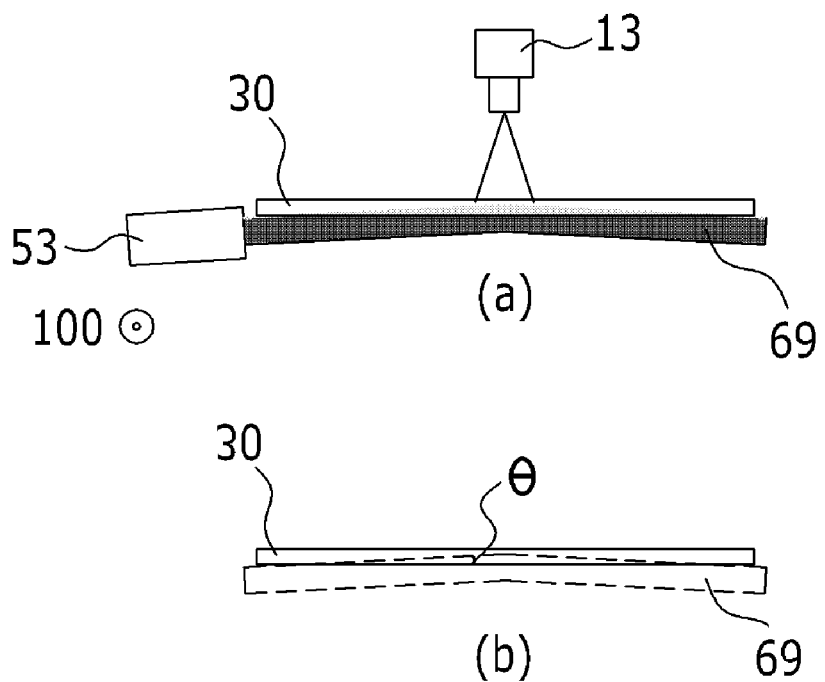
FIG. 2b is a sectional view of B-B' of FIG. 1.

FIG. 2b is a sectional view of a B-B' direction of FIG. 1. Referring to FIG. 2b, the apparatus for detecting particles on a glass surface in accordance with the present invention comprises a detection camera (hereinafter, a lower detection camera; 13) and another laser beam irradiator (hereinafter, a lower laser beam irradiator; 53) to exactly perceive on which side of the substrate (30) particles are attached.

Like the aforementioned upper laser beam irradiator (51), the lower laser beam irradiator (53) is disposed to make a lower laser beam irradiated in a direction vertical to the transferring direction of the glass substrate (30), and at this time, the lower laser beam (69) is diagonally irradiated as forming a predetermined inclination angle (θ) from a lower side of the glass substrate (30), and the inclination angle (θ) is configured to be incident at a low angle of 0.06° to 6°.

Namely, the upper laser beam irradiator (51) irradiates the upper laser beam (59) on the upper side of the glass substrate (30) by being installed in the vicinity of the upper side of the glass substrate (30), and the lower laser beam irradiator (53) irradiates the lower laser beam (69) on the lower side by being installed in the vicinity of the lower side of the glass substrate (30). More exactly, it can be known that the upper laser beam irradiator (51) irradiates the beam to the upper side of the glass substrate (30) by being positioned on a side of an upper part located outside a vertical extending area where the glass substrate (30) is positioned, and that the lower laser beam irradiator (53) irradiates the beam to the lower side of the glass substrate (30) by being positioned on a side of a lower part located outside the vertical extending area where the glass substrate (30) is positioned.

Like the upper detection camera (11), the lower detection camera (13) receives a beam diffused by particles existing on the glass substrate (30) after the lower laser beam (69) emitted from the lower laser beam irradiator (53) is irradiated on the lower side of the glass substrate (30).

Also, the lower detection camera (13) in accordance with a desirable embodiment of the present invention is disposed in an upper part of an area where the lower laser beam (69) is irradiated, but it is also possible to accomplish the same purpose even by disposing the camera under an area where the lower laser beam (69) is irradiated.

Moreover, the lower detection camera (13) is electrically connected to the detection signal processor (90), so that an image signal detected from the lower detection camera (13) is inputted to the detection signal processor (90).

Besides, the upper laser beam irradiator (51) and the lower laser beam irradiator (53) are disposed at predetermined intervals. In this case, if paths of each laser beam outputted from the upper and lower laser beams do not interfere with each other, any intervals can be possible.

The detection signal processor (90) analyzes/processes image signals detected from the upper detection camera (11) and the lower detection camera (13) when the upper laser beam (59) irradiated on the upper side of the glass substrate (30) and the lower laser beam (69) to be mentioned later are diffused by particles, and visually displays the analyzed/processed image signals, thereby distinguishing on which side of the glass substrate (30) the particles are attached and calculating size of the particles to notify a worker of the calculated size.

In a concrete way, the detection signal processor (90) provides one pair of 'particle display screens' that visually display information on the particles attached to the upper side or the lower side, based on the image signals inputted from the upper detection camera (11) and the lower detection camera (13). And, in detail, the one pair of the 'particle display screens' is divided into one pair of 'upper-particle display screens (11-81, 13-81) that provides information on particles (hereinafter, upper particles) attached to the upper side and one pair of 'lower-particle display screens' (11-91,13-91) that provides information on particles (hereinafter, lower particles) attached to the lower side.

That is to say, a worker can decide whether the particles detected through the one pair of these particle display screens provided from the detection signal processor (90) are attached to the upper side or the lower side of the glass substrate (30).

Figure 4:
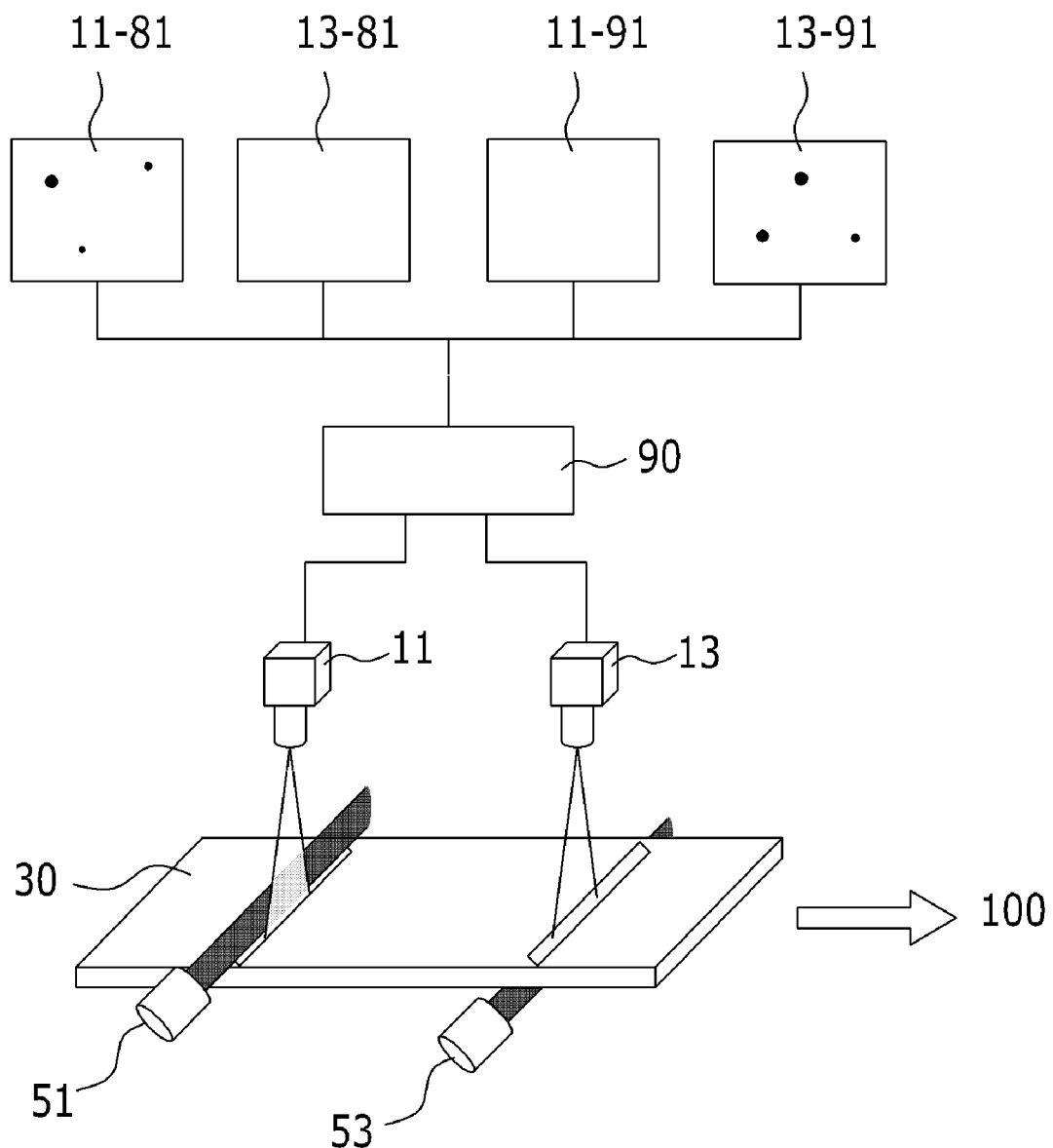
FIG. 4 is an embodiment for detecting particles attached to a glass substrate through an apparatus for detecting particles on a glass surface in accordance with the present invention and for visually displaying the detection process.

Referring to FIG. 4, first, the one pair of the upper-particle display screens shows detection images on particles attached to an upper side of a glass substrate (30), and one (11-81) is an example of an image screen where upper particles are generated/provided on the basis of an image signal detected by an upper detection camera (11), and the other (13-81) is an example of an image screen where the upper particles are created/provided on the basis of an image signal detected by a lower detection camera (13).

Next, the one pair of the lower-particle display screens (11-91,13-91) shows detection images on particles attached to a lower side of the glass substrate (30), and one (11-91) is an example of an image screen where lower particles are created/provided on the basis of an image signal detected by the upper detection camera (11), and the other (13-91) is an example of an image screen where the lower particles are created/provided according to an image signal detected by the lower detection camera (13).

In other words, the present invention provides images, that is, the particle-display screens to a worker, through a step of irradiating a laser beam on the upper side of the glass substrate (30) and receiving a beam diffused by the particles to output the beam as a video image, and a step of irradiating a laser beam on the lower side of the glass substrate (30) and receiving a beam diffused by the particles to output the beam as a video image. Thus, the worker can compare the image detected by the upper detection camera (11) with the image detected by the lower detection camera (13), thereby more exactly perceiving attached positions of the particles according to the results of which signal is more strongly displayed.

In addition, the aforementioned detection signal processor (90) is explained and described to provide the images themselves, which are generated based on the image signals inputted from the upper detection camera (11) and the lower detection camera (13), to the worker. Therefore, the worker can perceive existence of the particles and on which side of the glass substrate the particle are attached, by directly reading the provided images.

However, given that various image signals which can be inputted from the upper detection camera (11) and the lower detection camera (13) are set to conditional values, if a condition calculated by an image signal inputted to the detection signal processor (90) is matched with a preset condition of the detection signal processor (90), a result (that is, particle information) corresponding to the matched condition can be also outputted in character, numeral value, and image type by the detection signal processor (90).

The above conditional values, for instance, mean a condition of the particles being detected from the image signals, conditions in accordance with size of the detected particles, and a condition in accordance with which signal is more strongly displayed by comparing the image by the upper detection camera with the image by the lower detection camera.

In this case, the worker can immediately perceive the existence of the particles and on which side of the glass substrate the particles are attached, without directly reading the images provided from the detection signal processor (90).

Hereinafter, the functions of the apparatus for detecting particles on a glass surface of the present invention having the above configuration will be more specifically described.

Figure 3:
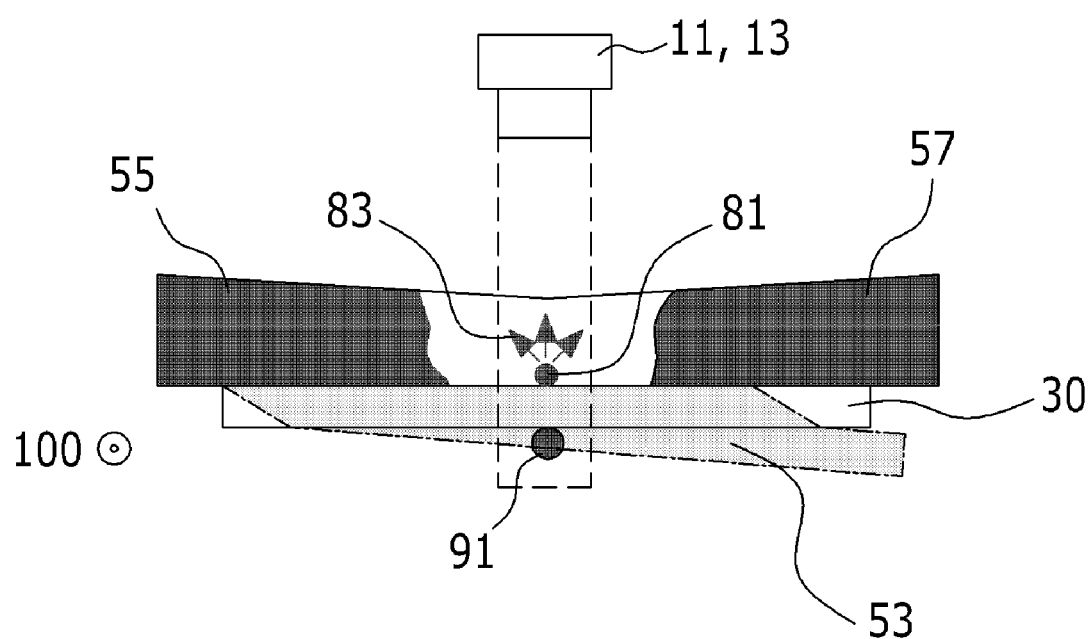
FIG. 3 is an embodiment for roughly illustrating paths of an upper laser beam irradiated on a glass substrate and particles attached to the glass substrate.

FIG. 3 is an embodiment for roughly illustrating paths of an upper laser beam (59) irradiated on a glass substrate (30) and particles attached to the glass substrate (30), and FIG. 4 is an embodiment for detecting particles attached to a glass substrate (30) through an apparatus for detecting particles on a glass surface in accordance with the present invention and for visually displaying the detection process.

As a reference, of the upper laser beam (59) illustrated in FIG. 4, shading of the inside of the laser beam of an area where particles (81) are located was omitted to clearly explain the functions of an upper laser beam (59) being diffused and reflected, Referring to FIG. 3 and FIG. 4, first, the upper laser beam (59) outputted from the upper laser beam irradiator (51) is irradiated in a direction vertical to a transferring direction of the glass substrate (30), and at this time, the laser beam has to be diagonally incident on an upper side of the glass substrate (30) as forming an inclination angle of 0.06° to 6° from the glass substrate (30).

Before explanation, the functions of the apparatus for detecting particles on a glass surface of the present invention will be described by supposing that particles (81,91) are attached to different positions of the upper and lower sides of the glass substrate (30), respectively.

For a more specific view of the upper laser beam (59) irradiated on the upper side of the glass substrate (30), the upper laser beam is composed of an incident beam (55) incident on the upper side of the glass substrate (30), a reflective beam (57) of the incident beam (55), which is reflected after reaching the upper side, and a transmissive beam (53) of the incident beam (55), which is transmitted on the lower side by permeating the glass substrate (30).

Likewise, the lower laser beam irradiated on the lower side of the glass substrate (30) is composed of an incident beam incident on the lower side of the glass substrate, a reflective beam of the incident beam, which is reflected after reaching the lower side, and a transmissive beam of the incident beam, which is transmitted on the upper side by permeating the glass substrate.

First, a detecting process and a detecting method for particles attached to the upper side of the glass substrate (30) basically comprise the steps of: a first step of irradiating the laser beam (59) on the upper side of the glass substrate (30) so that the beam arrives up to the other upper side from one upper side of the glass substrate (30); a second step of receiving a beam diffused by the particles after the laser beam (59) irradiated in the first step is irradiated on the upper side of the glass substrate (30); and a third step of deciding whether the particles exist on the glass substrate (30) by analyzing an image signal outputted from the second step.

To detect the particles existing on the lower side of the glass substrate, the following steps are further comprised, such as: a fourth step of irradiating the laser beam (69) on the lower side of the glass substrate (30) so that the beam arrives up to the other lower side by being irradiated from one lower side of the glass substrate; and a fifth step of receiving a beam diffused by the particles after the laser beam (69) irradiated in the fourth step is irradiated on the lower side of the glass substrate (30). And, in the above third step, it is also decided whether the particles, which are detected by analyzing image signals outputted in the second step and the fifth step, are attached to the upper side or the lower side of the glass substrate.

From now on, a specific method of detecting the particles existing on the glass substrate and of perceiving on which side of the glass substrate the detected particles exist will be described.

When the particles (81) moving by being attached to the upper side of the glass substrate (30) reach an area where the upper laser beam (59) is irradiated, a portion of the reflective beam (57) or the incident beam (55) of the upper laser beam is diffused (83) at random angle by the particles (81) attached to the upper side of the glass substrate (30), and the diffused beam is received in the upper detection camera (11) disposed in an upper part of the glass substrate (30).

'11-81' of FIG. 4 presents a particle-detection image screen where the upper laser beam diffused and reflected by the particles (81) attached to the upper side of the glass substrate (30) is sensed and displayed by the upper detection camera (11). Like shown in the drawing, the more beams are diffused and reflected, the larger particle-detection images are displayed, thereby visually notifying a worker that the particles (81) exist on the upper side of the glass substrate (30).

When the particles (81) moving by being attached to the upper side of the glass substrate (30) reach an area where the lower laser beam (69) is irradiated, by passing an area where the upper laser beam (59) is irradiated, the incident beam or the reflective beam of the lower laser beam (69) is not affected (that is, diffusion and reflection) by the upper particles. Therefore, most of the incident beam of the lower laser beam become reflective beams as they are, and are reflected outside, whereas only a relatively small amount of a laser beam of the incident beam is transmitted on the upper side of the glass substrate, leading diffusion and reflection by the upper particles.

Of the transmitted beam of the lower laser beam, the beam diffused and reflected by the upper particles is detected by the lower detection camera (13), and an image screen created/provided based on a detected image signal refers to '13-81' of FIG. 4. Since the transmitted beam of the lower laser beam has a relatively very small amount, diffusion signal strength of the upper particles caused by the transmitted beam is also deteriorated. As a result, like shown in '13-81' of FIG. 4, a detected image is displayed in generally dark blank state or shown as an unclear image form owing to very low resolution of the detected image on the particles.

Like mentioned above, the apparatus for detecting particles on a glass surface in accordance with the present invention individually comprises laser beam irradiators (51,53) for detecting the particles attached to the glass substrate (30), on an upper side and a lower side of the glass substrate (30) at predetermined intervals, and at this time, beams emitted from the laser beam irradiators are irradiated as forming predetermined inclination angles in a direction vertical to a transferring direction of the glass substrate (30), and it is exactly perceived on which side of the glass substrate (30) the particles sensed by the detection cameras (11,13) are attached, through particle-display screens provided through the above configuration.

Namely, in the case of the particles attached to the upper side of the glass substrate (30), a lot of laser beams (incident beams or reflective beams) are diffused/reflected as bumping into the upper particles in an area where the upper laser beam is irradiated, while a very small amount of laser beams (transmissive beams) are diffused and reflected by the upper particles in an area where the lower laser beam is irradiated. Thus, there are clear differences of diffusion signal strength sensed by the upper and lower detection cameras (11,13).

Accordingly, if a particle-detection image is clearly displayed on the upper-particle display screen (11-81) provided through the upper detection camera (11) while the image is displayed in generally dark blank state or in badly deteriorated resolution on the upper-particle display screen (13-81) provided through the lower detection camera (13), the worker can exactly perceive that the detected particles are located on the upper side of the glass substrate (30).

Since a detecting process and a detecting method of particles attached to the lower side of the glass substrate (30) are the same as the aforementioned detecting process and detecting method on the upper side, only the differences will be explained.

When the particles attached to the lower side of the glass substrate (30) move and reach the area where the upper laser beam (59) is irradiated, with the same reason that the upper particles reach the area of the lower laser beam (69), strength of a detected diffusion signal is very weak. As a result, like the lower-particle display screen (11-91) of FIG. 4, an image is displayed in generally dark blank state or in unclear state owing to badly deteriorated resolution of the displayed particles.

When the particles attached to the lower side of the glass substrate (30) move and reach the area where the lower laser beam (69) is irradiated by passing the irradiated area, with the same reason that the upper particles reach the area of the upper laser beam, strength of a detected diffusion signal is very increased, thereby clearly displaying the detected image on the particles on the lower-particle display screen (13-91) provided by the lower detection camera (13).

Hence, once the provided one pair of the lower-particle display screens (11-91,13-91) is displayed in the aforementioned type, the worker can exactly perceive that the particles are attached to the lower side of the glass substrate (30).

Figure 5:
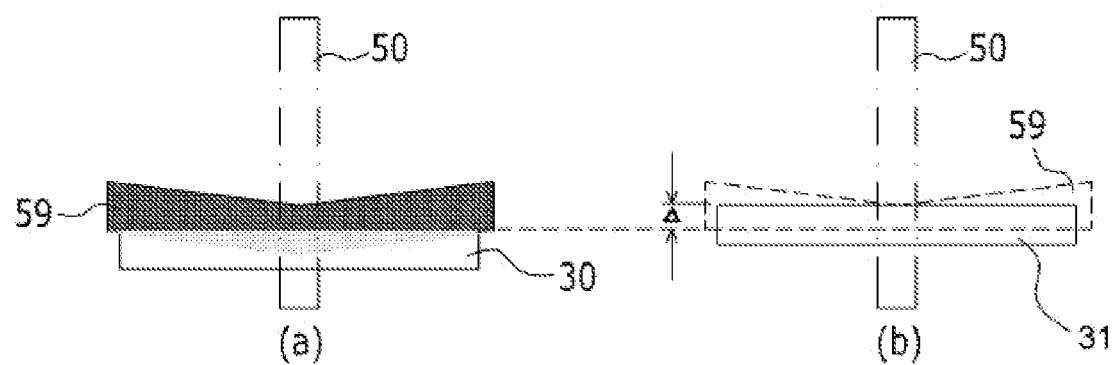
FIG. 5 is an operational diagram for illustrating a principle of exactly detecting particles on a glass surface regardless of changes of flatness of a glass substrate.

FIG. 5 is an operational diagram for illustrating a principle of exactly detecting particles on a glass surface regardless of changes of flatness of a glass substrate (30).

FIG. 5(a) illustrates that the transferred glass substrate (30) is being flatly transferred at a normal position. A glass substrate (31) shown in FIG. 5(b) is the glass substrate (31) whose flatness is changed, indicating that the glass substrate is being transferred while its flatness is changed as much as 'Δ' toward an upper part from the normal position. In addition, an area irradiated on an upper part of the glass substrate by the upper detection camera (11) is presented as a reference number '50'.

A prior apparatus for detecting particles on a glass surface has a problem that detective precision of particles attached to the glass substrate (30) gets more deteriorated since it does not properly cope with changes of flatness of the glass substrate (30), which occurs while the substrate is being transferred like above.

However, the apparatus for detecting particles on a glass surface in accordance with the present invention can minimize influence caused by changes of flatness of the substrate (30) during detection of the particles, because the laser beam (59) is irradiated from one side of the glass substrate (30) at a regular position all the time, even though the changes of the flatness of the glass substrate (30) occur.

More specifically, by referring to FIGS. 5(a) and (b), a detecting process for upper particles will be described as follows. Even though the glass substrate (30) reaching the area where the upper laser beam (59) is irradiated is positioned at a higher position (that is, position '31' of the glass substrate) by being upward-bent as much as 'Δ' from a perfectly flat position (that is, position '30' of the glass substrate), the upper side of the glass substrate (31) is still maintained in a state of being included in the inside of the upper laser beam (59), and accordingly, diffusion and reflection caused by the particles attached to the upper side of the glass substrate (30) can be also performed normally, resulting in an exact detection of the particles.

It is because, in the apparatus for detecting particles on a glass surface in accordance with the present invention, the upper laser beam (59) is irradiated in a direction vertical to the transferring direction of the glass substrate (30) while the upper laser beam (59) is diagonally incident as forming a predetermined inclination angle from the upper side of the glass substrate (30), which can allow the upper side of the glass substrate (31) to be always included in the inside (FIG. 7; Φ) in width direction of the laser beam even though changes of flatness occur as much as 'Δ' on the transferred glass substrate (30).

In accordance with the provisions of the patent statutes, the present invention has been described in what is considered to represent its preferred embodiment. However, it should be noted that the invention can be practiced otherwise than as specifically illustrated and described without departing from its spirit or scope.

What is claimed is:

1. A glass surface particle detecting apparatus for detecting particles existing on a surface of glass which is being transferred, comprising:
    an upper laser beam irradiator for irradiating a laser beam on an upper surface of glass in a first direction perpendicular to a second direction in which a glass substrate moves, wherein the laser beam is irradiated from one upper side of the glass substrate to other upper side of the glass substrate;
    an upper detection camera for receiving a beam diffused by particles after the laser beam irradiated in the upper laser beam irradiator is irradiated on an upper side of the glass substrate; and
    a detection signal processor for deciding whether the particles exist on the glass substrate by analyzing an image signal outputted from the upper detection camera.

2. The apparatus of claim 1, wherein the upper laser beam is diagonally incident as forming an inclination angle of 0.06° to 6° from the upper side of the glass substrate.

3. The apparatus of claim 1, wherein the upper laser beam and the lower laser beam have width (φ) defined in thickness direction of the glass substrate and thickness (T) defined in transferring direction of the glass substrate, and the laser beam is in oblong shape whose width (φ) is larger than thickness (T).

4. The apparatus of claim 1, the apparatus, further comprising:
    a lower laser beam irradiator for irradiating a laser beam on an lower surface of glass in the first direction perpendicular to the second direction in which the glass substrate moves, wherein the laser beam is irradiated from one lower side of the glass substrate to other lower side of the glass substrate;
    a lower detection camera for receiving a beam diffused by particles after the laser beam irradiated in the lower laser beam irradiator is irradiated on a lower side of the glass substrate; and wherein
    the detection signal processor decides on positions of the particles on the glass substrate by analyzing image signals outputted from the upper detection camera and the lower detection camera.

5. The apparatus of claim 4, wherein the detection signal processor provides particle-display screens that visually display information on the particles attached to the upper side or the lower side, based on the image signals inputted from the upper detection camera and the lower detection camera.

6. The apparatus of claim 4, wherein the upper laser beam is diagonally incident as forming an inclination angle of 0.06° to 6° from the upper side of the glass substrate.

7. The apparatus of claim 4, wherein the lower laser beam is diagonally incident as forming an inclination angle of 0.06° to 6° from the lower side of the glass substrate.

8. The apparatus of claim 4, wherein the upper laser beam and the lower laser beam have width (φ) defined in thickness direction of the glass substrate and thickness (T) defined in transferring direction of the glass substrate, and the laser beam is in oblong shape whose width (φ) is larger than thickness (T).

9. A glass surface's particle detecting method for detecting particles existing on a surface of glass which is being transferred, comprising the steps of:
    a first step of irradiating a laser beam on an upper surface of glass in a first direction perpendicular to a second direction in which a glass substrate moves, wherein the laser beam is irradiated from one upper side of the glass substrate to other upper side of the glass substrate;
    a second step of receiving a beam diffused by particles after the laser beam irradiated in the first step is irradiated on the upper surface of the glass substrate; and
    a third step of deciding whether the particles exist on the glass substrate by analyzing an image signal outputted in the second step.

10. The method of claim 9, the method, further comprising the steps of:
    a fourth step of irradiating a laser beam on a lower surface of glass in a first direction perpendicular to a second direction in which the glass substrate moves, wherein the laser beam is irradiated from one lower side of the glass substrate to other lower side of the glass substrate;
    a fifth step of receiving a beam diffused by particles after the laser beam irradiated in the fourth step is irradiated on the lower surface of the glass substrate; and wherein
    in the third step, it is decided whether the particles detected by analyzing image signals outputted in the second step and the fifth step are attached to the upper surface or the lower surface of the glass substrate.

11. A glass surface's particle detecting method for detecting whether particles existing on a surface of glass which is being transferred are attached to an upper side or a lower side of a glass substrate, comprising the steps of:
    a first step of irradiating a laser beam on an upper surface of glass in a first direction perpendicular to a second direction in which a glass substrate moves, wherein the laser beam is irradiated from one upper side of the glass substrate to other upper side of the glass substrate, and receiving a beam diffused by the particles to output the beam as a video image; and
    a second step of irradiating a laser beam on a lower surface of glass in a first direction perpendicular to a second direction in which the glass substrate moves, wherein the laser beam is irradiated from one lower side of the glass substrate to other lower side of the glass substrate, and receiving a beam diffused by the particles to output the beam as a video image.

* * * * *